US012575938B2

(12) United States Patent
Beale et al.

(10) Patent No.: US 12,575,938 B2
(45) Date of Patent: Mar. 17, 2026

(54) SPINAL IMPLANT SYSTEM AND METHOD

(71) Applicant: Warsaw Orthopedic, Inc., Warsaw, IN (US)

(72) Inventors: Jeffrey W. Beale, Bartlett, TN (US); Keith E. Miller, Germantown, TN (US); William Alan Rezach, Covington, TN (US); Richard A Hynes, Melbourne Beach, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 18/733,987

(22) Filed: Jun. 5, 2024

(65) Prior Publication Data

US 2024/0398578 A1     Dec. 5, 2024

Related U.S. Application Data

(63) Continuation of application No. 17/185,046, filed on Feb. 25, 2021, now Pat. No. 12,011,358, which is a
(Continued)

(51) Int. Cl.
| | |
|---|---|
| *A61F 2/44* | (2006.01) |
| *A61B 17/70* | (2006.01) |
(Continued)

(52) U.S. Cl.
CPC ............... *A61F 2/44* (2013.01); *A61B 17/70* (2013.01); *A61B 17/7077* (2013.01); *A61F 2/442* (2013.01); *A61F 2/4455* (2013.01); *A61F 2/4611* (2013.01); *A61F 2002/30171* (2013.01); *A61F 2002/30224* (2013.01); *A61F 2002/30232* (2013.01); *A61F 2002/30235*

(2013.01); *A61F 2002/30242* (2013.01); *A61F 2002/30299* (2013.01); *A61F 2002/305* (2013.01); *A61F 2002/30538* (2013.01); *A61F 2002/30556* (2013.01); *A61F 2002/30563* (2013.01); *A61F 2002/30607* (2013.01); *A61F 2002/30616* (2013.01); *A61F 2002/30841* (2013.01); *A61F 2002/30904* (2013.01);
(Continued)

(58) Field of Classification Search
CPC .......... A61F 2/44; A61F 2/442; A61F 2/4425; A61F 2/4611
USPC ........................ 606/246–249, 256–257, 279; 623/17.11–17.16
See application file for complete search history.

(56) References Cited

U.S. PATENT DOCUMENTS

| | | | |
|---|---|---|---|
| 5,649,926 A | 7/1997 | Howland | |
| 6,960,232 B2 * | 11/2005 | Lyons | ..................... A61F 2/442 |
| | | | 623/17.11 |
(Continued)

*Primary Examiner* — Eduardo C Robert
*Assistant Examiner* — Christina Negrellirodriguez
(74) *Attorney, Agent, or Firm* — Sorell, Lenna & Schmidt, LLP

(57) ABSTRACT

A method for treating a spine includes the steps of: creating a surgical pathway in a body along a first surgical approach to a surgical site including vertebral tissue; creating a surgical pathway in the body along a second surgical approach to the surgical site including the vertebral tissue; disposing a fulcrum with an intervertebral disc space of the vertebral tissue via the first surgical approach; and manipulating the vertebral tissue via the second surgical approach. Spinal implants, surgical instruments and systems are disclosed.

20 Claims, 8 Drawing Sheets

Related U.S. Application Data continuation of application No. 15/638,541, filed on Jun. 30, 2017, now Pat. No. 10,966,839.

(51) Int. Cl.
    *A61F 2/46*           (2006.01)
    *A61F 2/30*           (2006.01)

(52) U.S. Cl.
    CPC . *A61F 2002/443* (2013.01); *A61F 2002/4693* (2013.01); *A61F 2002/4694* (2013.01)

(56)                 References Cited

U.S. PATENT DOCUMENTS

| | | | |
|---|---|---|---|
| 7,655,008 B2 | 2/2010 | Lenke et al. | |
| 7,794,464 B2 | 9/2010 | Bridwell et al. | |
| 8,043,345 B2 | 10/2011 | Carl et al. | |
| 8,172,880 B2 * | 5/2012 | Graf .................... | A61F 2/4405 |
| | | | 606/257 |
| 8,277,490 B2 | 10/2012 | Freeman et al. | |
| 2007/0213715 A1 | 9/2007 | Bridwell et al. | |
| 2009/0005874 A1 * | 1/2009 | Fleischmann ........... | A61F 2/442 |
| | | | 623/17.11 |
| 2011/0160861 A1 | 6/2011 | Jimenez et al. | |
| 2011/0172714 A1 | 7/2011 | Adjei et al. | |
| 2011/0257690 A1 | 10/2011 | Rezach | |
| 2012/0136444 A1 * | 5/2012 | Ferree .................... | A61F 2/442 |
| | | | 623/17.16 |
| 2014/0114414 A1 | 4/2014 | Abdou et al. | |
| 2015/0018886 A1 | 1/2015 | Ali | |
| 2016/0007983 A1 | 1/2016 | Frey et al. | |
| 2016/0022438 A1 | 1/2016 | Lamborne et al. | |
| 2016/0067056 A1 | 3/2016 | Armstrong et al. | |
| 2017/0325970 A1 * | 11/2017 | Abdou .............. | A61B 17/7079 |

* cited by examiner

SPINAL IMPLANT SYSTEM AND METHOD

CROSS REFERENCE TO RELATED APPLICATIONS

This application is a continuation of U.S. patent application Ser. No. 17/185,046, filed Feb. 25, 2021, which is a continuation of U.S. patent application Ser. No. 15/638,541, filed Jun. 30, 2017, now U.S. Pat. No. 10,966,839. These applications are expressly incorporated by reference herein, in their entireties.

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative disc disease, disc herniation, osteoporosis, spondylolisthesis, stenosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, bone screws, rods and interbody implants can be delivered to a surgical site for fixation with bone to immobilize a joint. Such spinal constructs can be employed with bone growth promoting material to enhance fixation of the implants with the bone. This disclosure describes an improvement over these prior technologies.

SUMMARY

In one embodiment, a method for treating a spine is provided. The method comprises the steps of: creating a surgical pathway in a body along a first surgical approach to a surgical site including vertebral tissue; creating a surgical pathway in the body along a second surgical approach to the surgical site including the vertebral tissue; disposing a fulcrum with an intervertebral disc space of the vertebral tissue via the first surgical approach; and manipulating the vertebral tissue via the second surgical approach. In some embodiments, spinal implants, surgical instruments and systems are provided.

In one embodiment, a spinal implant system is provided. The spinal implant system includes a spinal implant comprising a body including a first vertebral engaging surface and a second vertebral engaging surface being disposable with an intervertebral disc space. Bone graft is disposable with the intervertebral disc space. A fulcrum is disposable with the intervertebral disc space. A surgical instrument is engageable with one or more vertebra disposed adjacent the intervertebral disc space.

In one embodiment, a spinal implant is provided. The spinal implant includes an expandable spinal implant comprising a body including a first vertebral engaging surface and a second vertebral engaging surface being disposable with an intervertebral disc space. A fulcrum is disposable with a selected portion of the intervertebral disc space and engageable with vertebral tissue to facilitate rotation of one or more vertebra and maintain disc height.

BRIEF DESCRIPTION OF THE DRAWINGS

The present disclosure will become more readily apparent from the specific description accompanied by the following drawings, in which.

DETAILED DESCRIPTION

Figure 1:
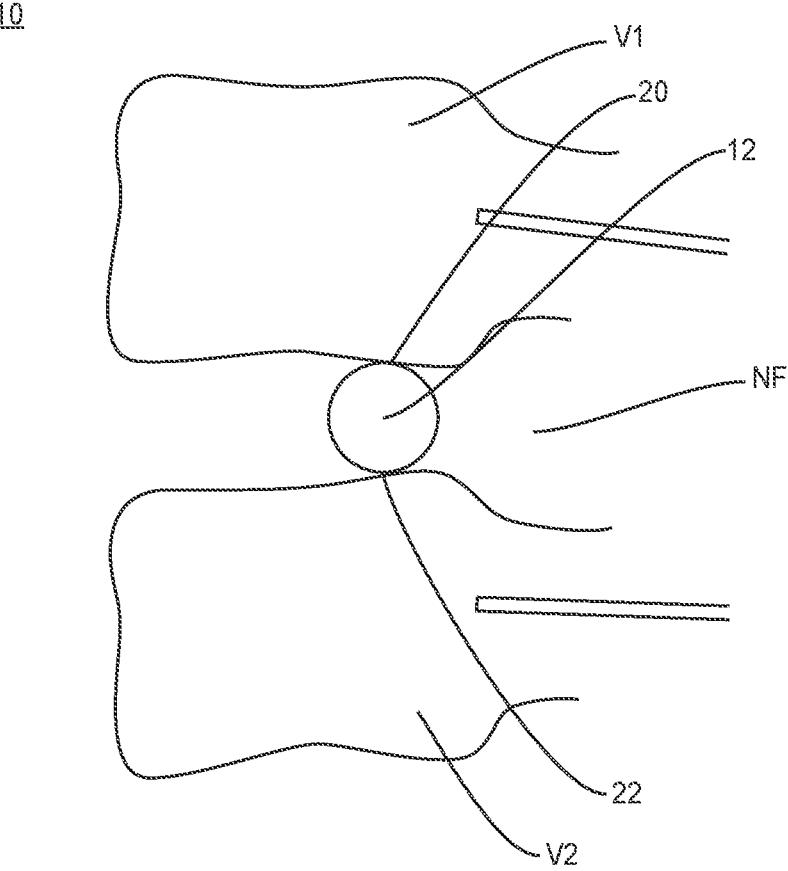
FIG. 1 is a side view of components of one embodiment of a surgical system in accordance with the principles of the present disclosure disposed with vertebrae.
Figures 2, 3, 4, 5, 6:
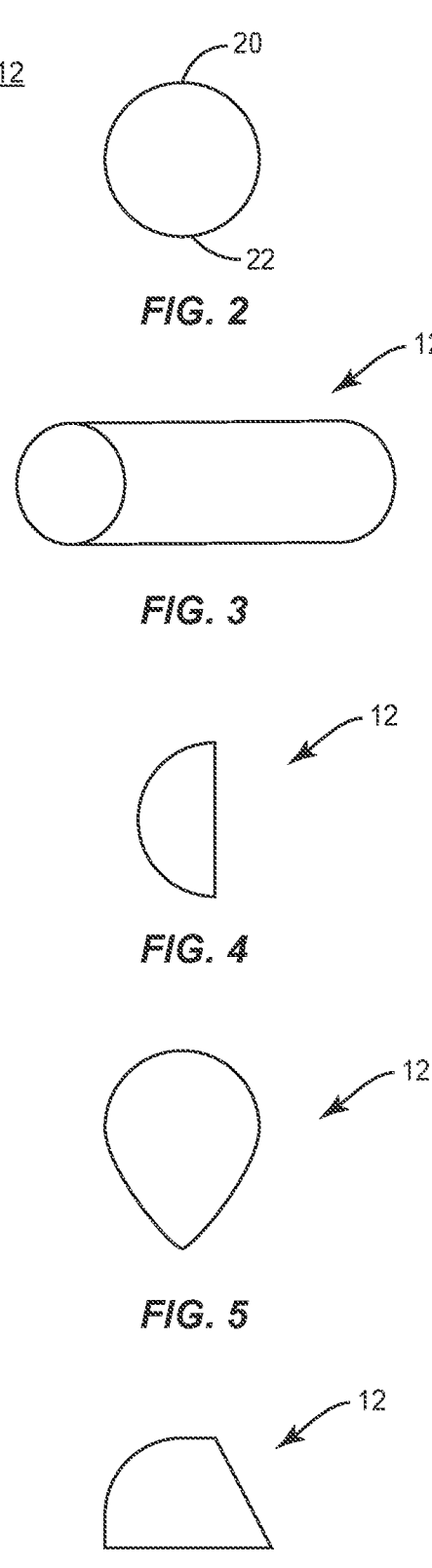
FIG. 2 is a side view of components of one embodiment of a surgical system in accordance with the principles of the present disclosure.
FIG. 3 is a perspective view of components of one embodiment of a surgical system in accordance with the principles of the present disclosure.
FIG. 4 is a side view of components of one embodiment of a surgical system in accordance with the principles of the present disclosure.
FIG. 5 is a side view of components of one embodiment of a surgical system in accordance with the principles of the present disclosure.
FIG. 6 is a side view of components of one embodiment of a surgical system in accordance with the principles of the present disclosure.
Figure 7:
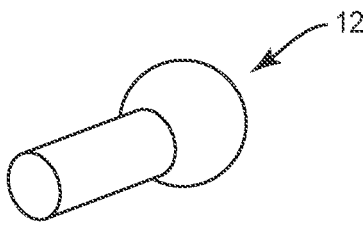
FIG. 7 is a perspective view of components of one embodiment of a surgical system in accordance with the principles of the present disclosure.
Figure 8:
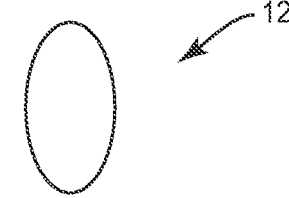
FIG. 8 is a side view of components of one embodiment of a surgical system in accordance with the principles of the present disclosure.
Figure 9:
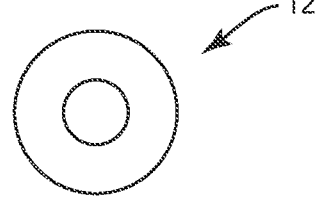
FIG. 9 is a side view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and/or a surgical instrument, and a method for treating a spine.

In some embodiments, the present system comprises a surgical device that includes a fulcrum. In some embodiments, the fulcrum is configured for use during a simultaneous access and/or sequential access surgical procedure. In some embodiments, the fulcrum is configured to facilitate restoration of a natural lordotic curve to a straight or kyphotic spine. In some embodiments, this configuration resists and/or prevents a decrease in neural foraminal height during a surgical procedure.

In some embodiments, the present system comprises a fulcrum that can be inserted, manipulated and/or facilitates access for one or a plurality of surgical approaches, such as, for example, an anterior approach, a posterior approach, a lateral approach, posterior mid-line approach, direct lateral approach, postero-lateral approach, antero-lateral approach, and/or combinations thereof in connection with access procedures. In some embodiments, the present system comprises a fulcrum that is employed with a simultaneous access and/or sequential access surgical procedure that includes one or a plurality of surgical approaches, and/or combinations thereof, as described herein. In some embodiments, the present system comprises a fulcrum that is employed with a simultaneous access surgical procedure for disposal of the fulcrum in an intervertebral disc space while performing a posterior compression. In some embodiments, the fulcrum can be disposed with the disc space for optimal lordosis or kyphosis. In some embodiments, the fulcrum utilizes posterior compression to maintain a neural for aminal height. In some embodiments, the fulcrum facilitates providing curvature correction, such as, for example, opening an anterior disc space by leveraging about the fulcrum while maintaining a selected disc height, such as, for example, a posterior disc height and neural for aminal height. In some embodiments, the present system can comprise one or more fulcrum surgical devices of various configurations and sizes for insertion into an intervertebral disc space. In some embodiments, the fulcrum configuration can be varied by dilation of additional instruments. In some embodiments, simultaneous access is facilitated by posterior compression/distraction of the fulcrum in the disc space. In some embodiments, the present fulcrum is employed with a plurality of surgical pathways and/or approaches, as described herein and for example, a posterior portion of a patient and a lateral portion of a patient accessed during one or more spinal procedures, for example, in connection with simultaneous access.

In some embodiments, the present system comprises a fulcrum that includes an expandable implant. In some embodiments, the present system comprises expanding instruments configured and utilized as a fulcrum. In some embodiments, the present system comprises a fulcrum including biomaterials and other materials, such as, for example, hard, soft, layered and/or combinations thereof. In some embodiments, the present system comprises a fulcrum utilized either by itself or in combination with instruments and/or implants, such as, for example, posterior compressors or disc space distractors to distribute load more evenly. In some embodiments, the present system comprises one or multiple fulcrums configured to seesaw a disc space slowly to achieve a selected disc height. In some embodiments, the present system comprises a surgical device that includes a fulcrum integral with a spinal implant, separate and not attached with a spinal implant, and/or added to a spinal implant. In some embodiments, the present system comprises a surgical device that includes a distal fulcrum extending from a spinal implant. In some embodiments, the distal fulcrum includes a PEEK extension integral and/or molded with a PEEK interbody cage, and the extension comprises a fulcrum engageable for simultaneous manipulation of the extension and the interbody cage.

In some embodiments, the present system comprises a fulcrum configured to uniformly and/or evenly distribute loads when restoring a spine to a selected condition, such as, for example, a disc height and/or a sagittal alignment through a simultaneous access procedure. In some embodiments, the present system comprises a fulcrum employed with a method for treating a spine that includes the step of placing a fulcrum within a disc space to facilitate precise curvature correction while maintaining a selected disc height and/or a selected neural for aminal height.

In some embodiment, the present system comprises a fulcrum that includes a surface texture configured to grip a vertebral endplate. In some embodiments, the fulcrum can include projections, such as, for example, teeth configured to reduce spondylolisthesis and/or engage tissue. In some embodiments, the fulcrum can include an expanding, hinged and/or modular surgical device, and/or include a spheroidal joint. In some embodiments, the fulcrum may include various surface configurations, such as, for example, hard, soft, layered, or a combination thereof. In some embodiments, the fulcrum may include biological materials and/or remain in the disc space as all or portion of the interbody device. In some embodiments, the fulcrum includes a surface geometry, such as, for example, directional teeth configured to engage tissue to reduce spondylolisthesis. In some embodiments, the teeth are configured to facilitate engagement with tissue during compression. In some embodiments, the teeth may facilitate motion in one direction while resisting and/or preventing motion in other directions. In some embodiments, the teeth may augment the surgeon's ability to correct deformities by encouraging translation of adjacent vertebral bodies in a selected direction. In some embodiments, the fulcrum includes a mating surface geometry such that the fulcrum is modular and configured for a snap-on engagement with one or more snap-on parts of the surgical device.

In some embodiments, the fulcrum may be harder or softer than tissue. In some embodiments, the fulcrum may include biologically-active materials such that the fulcrum can remain in the disc space. In some embodiments, the fulcrum can be utilized with an interbody implant or remain separate from the interbody implant. In some embodiments, the fulcrum may be expandable, hinged, or multiple parts joined at a ball and socket joint. In some embodiments, the fulcrum may include an expandable fulcrum with modular sized and/or adjustable parts or balloons.

In some embodiments, the present system is employed with a method including the steps of creating a surgical pathway in a body along a first surgical approach to a surgical site including vertebral tissue, creating a surgical pathway in the body along a second surgical approach to the surgical site including the vertebral tissue, disposing a fulcrum with an intervertebral disc space of the vertebral tissue via the first surgical approach and manipulating the vertebral tissue via the second surgical approach. In some embodiments, the method includes the step of inserting a fulcrum at any point along an anterior/posterior direction within a disc space. In some embodiments, the method includes the step of inserting a fulcrum eccentrically within a disc space. In some embodiments, fulcrum placement determines motion and/or articulation of surrounding structures about the fulcrum. In some embodiments, the fulcrum may be utilized with graft material and an expandable interbody. In some embodiments, an endplate distractor may be utilized in conjunction with the fulcrum. In some embodiments, the method includes the step of gross manipulation of a body. In some embodiments, the step of gross manipulation of a body includes positioning, manipulating and/or orienting the body with a surgical or operating room table in an operating room such that a spine of the body is similarly positioned, manipulated and/or oriented. In some embodiments, the step of gross manipulation of a body includes a surgeon and/or operating room personnel manually positioning, manipulating and/or orienting the body with a table in an operating room such that a spine of the body is similarly positioned, manipulated and/or oriented. In some embodiments, the step of manipulating the vertebral tissue includes aligning the vertebral tissue with a surgical instrument and the method further includes the step of gross manipulating a body, as described herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-11, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a surgical device and/or a spinal implant, as described herein, may be formed substantially of a biocompatible metal, such as titanium and selectively coated with a bone-growth promoting material, such as HA. In one embodiment, a surgical device and/or a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the surgical device and/or spinal implant to modify a radiographic signature of the surgical device and/or spinal implant, and/or improve bony ongrowth to the surgical device or spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce surgical devices, surgical instrumentation and/or spinal implants at a surgical site within a body of a patient, which includes, for example, vertebrae. In some embodiments, the components of spinal implant system 10 are employed in connection with surgical treatment that includes access to a surgical site by one or a plurality of surgical approaches. For example, the components of spinal implant system 10 can be employed with spinal procedures that include access during a single procedure, sequential access and/or simultaneous access to a surgical site including vertebral tissue, one or a plurality of surgical approaches and/or surgical pathways including one or more incisions within a sterile boundary. In some embodiments, the implant can include spinal constructs having, such as, for example, interbody devices, interbody cages, bone fasteners, spinal rods, tethers, connectors, plates and/or bone graft. In some embodiments, spinal implant system 10 is employed to achieve consistent, measured lordosis in a spinal segment of vertebrae to be corrected and fused, resist and/or prevent inducement of kyphosis, facilitate sagittal alignment, and/or avoid the influence of PI-LL mismatch and/or closing of the neural foramen, which can lead to, for example, iatrogenic neural symptoms and nerve root impingement. In some embodiments, spinal implant system 10 is employed to utilize the strength properties of a vertebral endplate, which resists and/or prevents subsidence and kyphosis. The surgical procedure can include surgical treatment of a cervical, thoracic, lumbar and/or sacral region of a spine.

Spinal implant system 10 includes a surgical device comprising a fulcrum 12 disposable with an intervertebral disc space, as described herein, to facilitate selected curvature restoration and to maintain a selected disc and/or neural for aminal height. In some embodiments, fulcrum 12 can comprise a surgical instrument, a spinal implant and/or a surgical device employed with surgical instruments and spinal implants. In some embodiments, fulcrum 12 can be employed in connection with various access procedures to one or a plurality of surgical approaches for compression/distraction maneuvers, leveraging vertebrae, distributing loads across vertebrae, and/or selective placement to determine motion and/or articulation of surrounding structures about fulcrum 12.

Fulcrum 12 includes a vertebral engaging surface 20 and a vertebral engaging surface 22. Fulcrum 12 is utilized to facilitate restoration of a natural lordotic curve to a straight kyphotic spine without decreasing a height of a neural foramen NF. In some embodiments, fulcrum 12 includes a circular configuration. In some embodiments, fulcrum 12 includes various configurations to facilitate rotation of vertebrae V1, V2 relative to fulcrum 12. In some embodiments, fulcrum 12 can include various sizes. In some embodiments, fulcrum 12 can include various lengths. In some embodiments, fulcrum 12 includes various configurations, such as, for example, tubular (FIG. 3), half-moon (FIG. 4), tear drop (FIG. 5), trapezoidal with a radius (FIG. 6), spherical with a tubular extension (FIG. 7), oval (FIG. 8), tubular having a hollow cavity (FIG. 9), oblong, rectangular, polygonal, irregular, uniform, non-uniform, variable or tapered. In some embodiments, fulcrum 12 includes a first portion having a first height and a second portion having a second height, for example, stepped, tapered, angled, staggered, offset or undulating, for example, to facilitate coronal correction of vertebrae.

Figure 10:
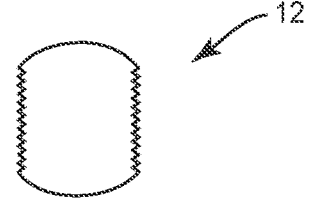
FIG. 10 is a side view of components of one embodiment of a surgical system in accordance with the principles of the present disclosure.
Figure 11:
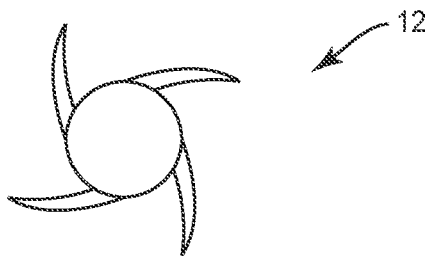
FIG. 11 is a side view of components of one embodiment of a surgical system in accordance with the principles of the present disclosure.

In some embodiments, fulcrum 12 includes various surface configurations, such as, for example, textured (FIG. 10). In some embodiments, fulcrum 12 may include one or more teeth oriented in a selected direction (FIG. 11). In some embodiments, the teeth are configured to facilitate a direction of engagement of fulcrum 12 with vertebral tissue. In some embodiments, the teeth are elongated to facilitate engagement with tissue during compression.

Figure 12:
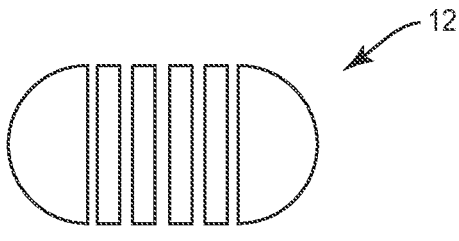
FIG. 12 is a side view of components of one embodiment of a surgical system in accordance with the principles of the present disclosure.
Figure 13:
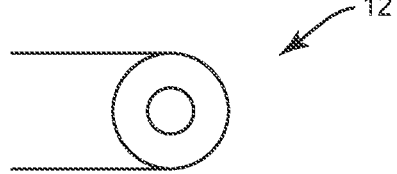
FIG. 13 is a side view of components of one embodiment of a surgical system in accordance with the principles of the present disclosure.
Figure 14:
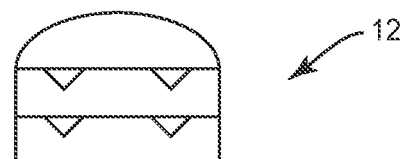
FIG. 14 is a side view of components of one embodiment of a surgical system in accordance with the principles of the present disclosure.
Figure 15:
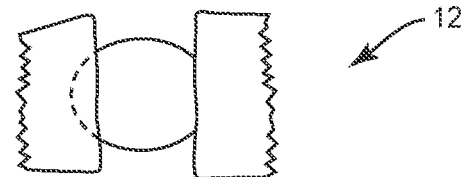
FIG. 15 is a side view of components of one embodiment of a surgical system in accordance with the principles of the present disclosure.
Figure 16:
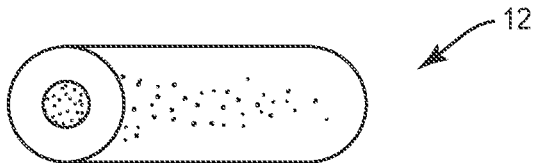
FIG. 16 is a perspective view of components of one embodiment of a surgical system in accordance with the principles of the present disclosure.

In some embodiments, fulcrum 12 can comprise biological materials that remain within the vertebral space after compression. In some embodiments, fulcrum 12 is configured to expand (FIG. 12). In some embodiments, fulcrum 12 may include various components to facilitate expansion, such as, for example, shims, obturators, dilators, a mechanical expanding mechanism, balloons and/or expansion elements in multiple directions. In some embodiments, fulcrum 12 is configured with a hinged connection (FIG. 13). In some embodiments, fulcrum 12 is configured as a modular component configured for a snap-fit connection with one or more alternate components (FIG. 14). In some embodiments, fulcrum 12 is configured to include a mobile bearing element (FIG. 15). In some embodiments, fulcrum 12 can include various surface configurations, such as, for example, a surface that is hard, soft, layered or a combination thereof (FIG. 16).

In some embodiments, spinal implant system 10 is employed with a simultaneous access surgical approach, technique or procedure. In some embodiments, spinal implant system 10 is employed with a surgical approach, technique or procedure, which utilizes an opening in bone, such as, for example, foramina between a vertebral body, such as, for example, vertebra V1 and a vertebral body, such as, for example, vertebra V2. For example, utilizing a first surgical approach S1, such as, for example, a lateral approach to position fulcrum 12 with a posterior portion P of vertebrae V1, V2, rotating the patient and utilizing a second surgical approach S2, such as, for example, a posterior approach to sagitally align fulcrum 12 with vertebra V1, V2. In some embodiments, the patient and/or vertebrae are rotated via gross manipulation of the patient body. For example, gross manipulation of the patient body can include positioning, manipulating and/or orienting the body, with a mechanical, motorized, automated and/or computer controlled surgical table or manually via a surgeon and/or operating room personnel, in an operating room such that a spine of the body is similarly positioned, manipulated and/or oriented.

In some embodiments, spinal implant system 10 is employed with a patient in a prone and lateral position, and/or employed with various additional surgical approaches to the spine, including anterior, posterior, posterior mid-line, direct lateral, postero-lateral, and/or antero-lateral approaches. In some embodiments, fulcrum 12 could be used in procedures for the treatment of any selected levels of the human spine, including the cervical spine, thoracic spine and/or lumbar spine (including but not limited to the L5-S1 (lumbosacral) disc space.

A medical practitioner makes and/or creates an incision in tissue, which includes soft tissue and/or muscle, to create a surgical pathway along first surgical approach S1. A medical practitioner makes and/or creates an incision in tissue, which includes soft tissue and/or muscle, to create a surgical pathway along second surgical approach S2. Once access to the surgical site is obtained, a surgical procedure, as described herein, is performed for treating the spine disorder. The diseased and/or damaged portions of vertebrae V, which may include diseased and/or damaged intervertebral disc tissue, are removed to create a vertebral space between vertebrae V1, V2.

Figure 17:
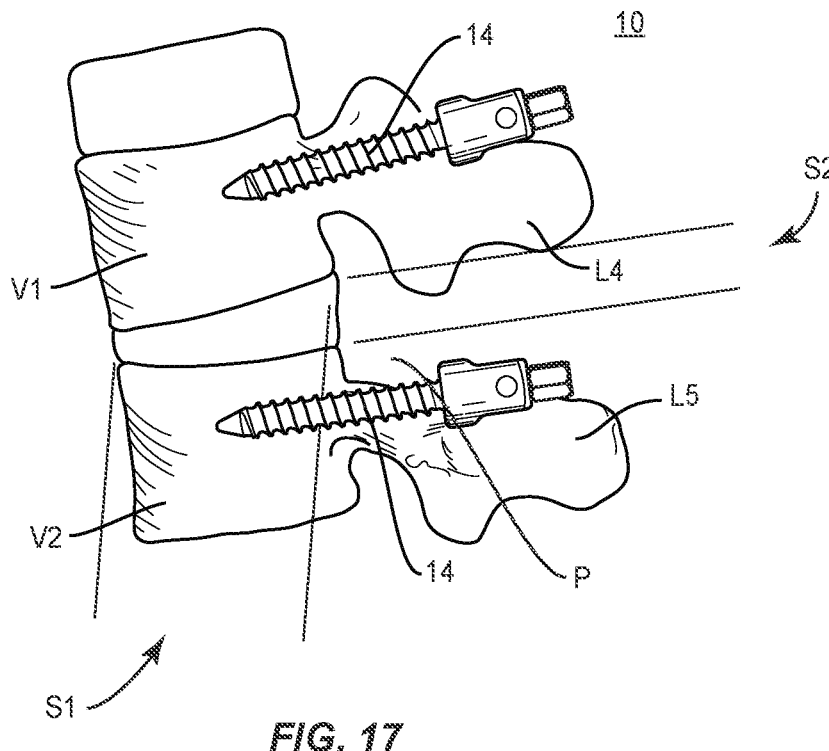
FIG. 17 is a side view of components of one embodiment of a surgical system in accordance with the principles of the present disclosure disposed with vertebrae.
Figure 18:
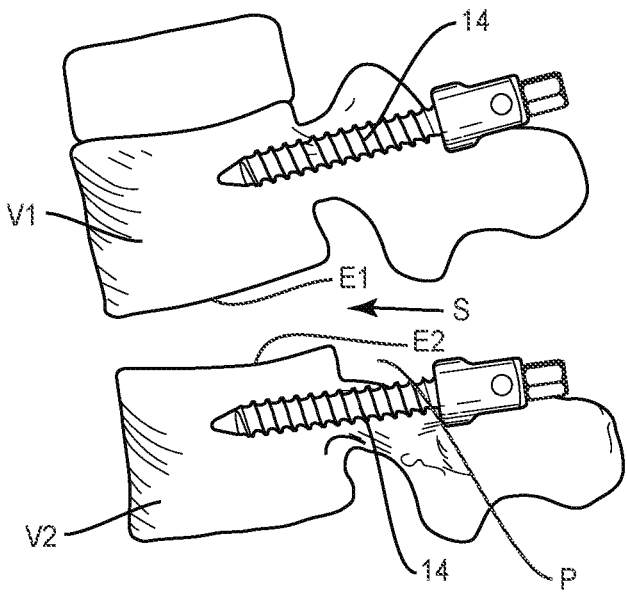
FIG. 18 is a side view of components of one embodiment of a surgical system in accordance with the principles of the present disclosure disposed with vertebrae.
Figure 19:
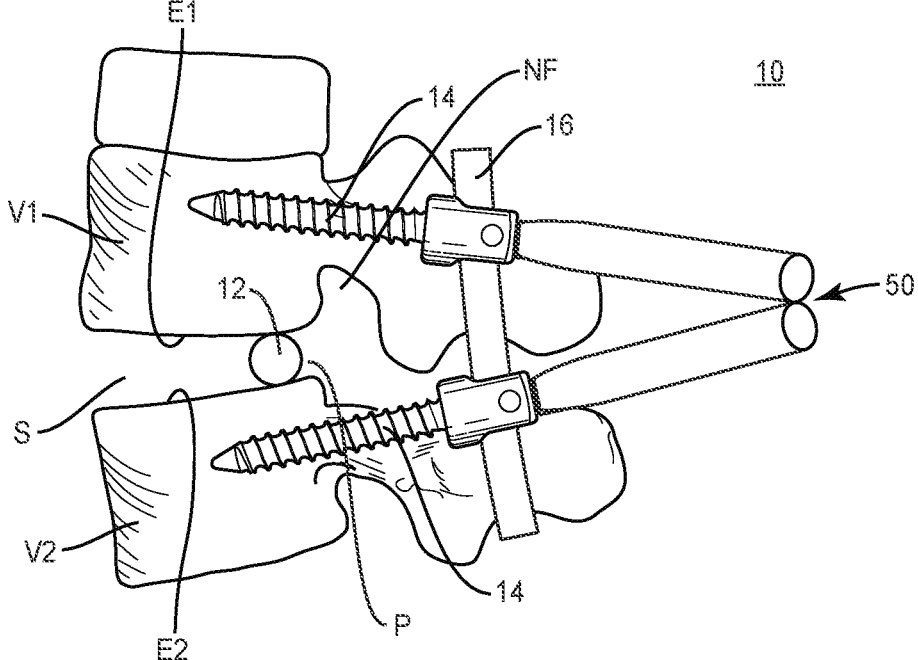
FIG. 19 is a side view of components of one embodiment of a surgical system in accordance with the principles of the present disclosure disposed with vertebrae.

In some embodiments, pilot holes are made in selected vertebra of vertebrae V for receiving fixation elements, such as, for example, bone fasteners 14. For example, bone fasteners 14 are inserted or otherwise engaged with each of vertebrae V1, V2. In some embodiments, spinal constructs including rods 16 are employed as provisional and/or working rods to support vertebrae V during a surgical procedure, as shown in FIGS. 17-19. One or more rods 16 are connected and reduced with receivers of the bone fasteners to provide support and stabilization of vertebrae V1, V2. In some embodiments, spinal implant system 10 may include one or a plurality of the spinal constructs. In some embodiments, the plurality of spinal constructs may be disposed in various alternate orientations, such as, for example, side by side, parallel, transverse and/or other angular orientations such as acute or obtuse, co-axial and/or may be offset or staggered. In some embodiments, the plurality of spinal constructs including rods 16 may provide a template configuration for permanently implantable spinal rods, such as, implantable, final, permanent, removable, non-removable, bio-absorbable, resorbable and/or bio-degradable, and/or comprise permanently implantable spinal rods.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. In some embodiments, vertebral facets are resected. A discectomy is performed to create vertebral space S between vertebral bodies V1, V2, as shown in FIG. 18.

In some embodiments, fulcrum 12 comprises a surgical device configured as a surgical instrument 12. Fulcrum/surgical instrument 12 is utilized for compression and/or distraction maneuvers and/or leveraging vertebrae V1, V2, as shown in FIG. 19. In some embodiments, fulcrum/surgical instrument 12 is visualized by fluoroscopy and oriented before introduction into vertebral space S. A surgical instrument, such as, for example, an inserter (not shown) is connected with fulcrum/surgical instrument 12 for disposal in an introduction or delivery of fulcrum/surgical instrument 12 along a lateral surgical approach S1. Fulcrum/surgical instrument 12 is steerable to vertebral space S between vertebrae V1, V2 along surgical approach S1. In some embodiments, manipulation of the inserter rotates and/or steers fulcrum 12. Fulcrum/surgical instrument 12 is disposed posteriorly within vertebral space S adjacent posterior portion P. In some embodiments, fulcrum/surgical instrument 12 could be placed at any point along an anterior/posterior direction within intervertebral space S. Changing the placement of fulcrum/surgical instrument 12 alters the way that the surrounding structures articulate about fulcrum/surgical instrument 12.

A compressor/distractor 50 is connected with vertebrae V1, V2 along a posterior surgical approach S2. Compressor/distractor 50 manipulates vertebrae V1, V2 such that endplate surfaces E1, E2 adjacent posterior portion P engage fulcrum/surgical instrument 12. For example, manipulating compressor/distractor 50 causes endplate surfaces E1, E2 adjacent posterior portion P to exert a compressive or distraction force on fulcrum/surgical instrument 12 such that vertebrae V1, V2 are selectively rotated about fulcrum/surgical instrument 12 to achieve a measured lordosis in vertebrae V1, V2. Fulcrum/surgical instrument 12 and compressor/distractor 50 facilitate rotation of vertebrae V1, V2 while resisting and/or preventing compression of posterior portion P and neural foramen NF. Fulcrum 12 restores the natural lordotic curve to a straight kyphotic spine without decreasing the height of a neural foramen NF and avoiding a resulting compression of the nerve root. In some embodiments, the patient body and/or vertebrae can be rotated via gross manipulation of the patient body, as described herein, and/or to facilitate aligning and/or manipulating vertebral tissue, as described herein, with fulcrum/surgical instrument 12. In some embodiments, the patient body and/or vertebrae can be rotated via gross manipulation of the patient body, as described herein, and/or to facilitate aligning and/or manipulating vertebral tissue, as described herein, with or without a surgical instrument.

Figure 20:
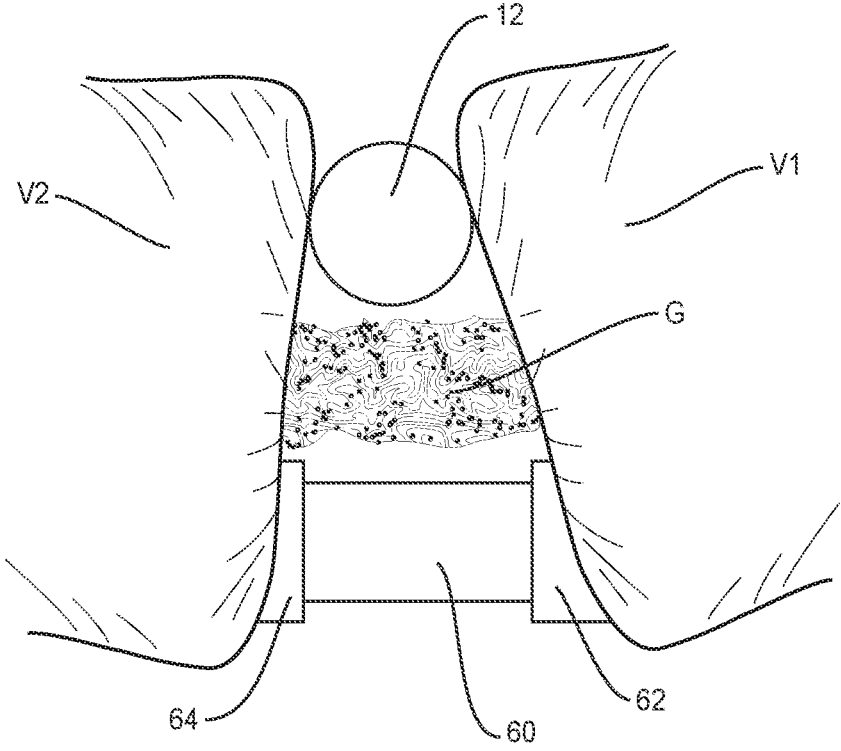
FIG. 20 is a side view of components of one embodiment of a surgical system in accordance with the principles of the present disclosure disposed with vertebrae.

Fulcrum/surgical instrument 12 is removed from vertebral space S. An interbody implant 60 is disposed with vertebrae V1, V2, as shown in FIG. 20. Implant 60 includes a vertebral engaging surface 62 and a vertebral engaging surface 64. Implant 60 is disposed with vertebral space S. In some embodiments, implant 60 includes a solid configuration. In some embodiments, bone graft is disposed with intervertebral space S to enhance fixation of the components and/or surfaces of implant 60 with vertebrae V1, V2. In some embodiments, bone graft may be disposed, packed, coated or layered within, on, adjacent or about the components and/or surfaces of implant 60.

In some embodiments, fulcrum 12 comprises a surgical device configured as an interbody implant, as an alternate embodiment of fulcrum 12 shown in FIG. 19. Fulcrum/ implant 12 remains within vertebral space S after manipulation of vertebrae V1, V2, similar to that described herein with regard to fulcrum 12. Fulcrum/implant 12 is selectively positioned to an implantable orientation adjacent a posterior portion P of vertebral space S between vertebrae V1, V2 along one or more surgical approaches, as described herein. Fulcrum/implant 12 is sagittally aligned with vertebrae V1, V2. In some embodiments, posterior placement of fulcrum/ implant 12 provides space within vertebral space S for disposal of bone graft and/or other agents, as described herein. Posterior placement of fulcrum/implant 12 improves stability and decreases the risk of subsidence into tissue, as described herein. In some embodiments, fulcrum/implant 12 provides height restoration between vertebral bodies, decompression, and restoration of sagittal and/or coronal balance. In some embodiments, fulcrum/implant 12 could be placed at any point along an anterior/posterior direction within intervertebral space S. Fulcrum 12 is inserted into vertebral space S between vertebrae V1, V2 to re-establish and maintain a selected disc height. In some embodiments, this configuration of fulcrum/implant 12 and selective orientation of fulcrum/implant 12 with vertebrae V1, V2 aligns fulcrum/implant 12 with the portion of a vertebral endplate having a higher strength and resistance to subsidence.

Compressor/distractor 50 is connected with vertebrae V1, V2 along surgical approach S2, as shown in FIG. 19. Compressor/distractor 50 manipulates vertebrae V1, V2 such that endplate surfaces E1, E2 adjacent posterior portion P engage fulcrum/implant 12. For example, manipulating compressor/distractor 50 causes endplate surfaces E1, E2 adjacent posterior portion P to exert a compressive or distraction force on fulcrum/implant 12 such that vertebrae V1, V2 are selectively rotated about fulcrum/implant 12 to achieve a measured lordosis in vertebrae V1, V2. Fulcrum/ implant 12 is positioned to resist and/or prevent compression of neural foramen F. As such, fulcrum/implant 12 is employed to achieve segmental lordosis and resist and/or prevent closing of neural foramen F to avoid resulting compression of the nerve root.

In some embodiments, implant 60, as described herein with regard to FIG. 20, is disposed with vertebral space S in conjunction with fulcrum/implant 12. In some embodiments, implant 60 includes an interlocking connection with fulcrum/implant 12. In some embodiments, bone graft G is disposed with intervertebral space S between fulcrum/implant 12 and implant 60 to enhance fixation of the components and/or surfaces of fulcrum/implant 12 and/or implant 60 with vertebrae V1, V2. In some embodiments, bone graft G may be disposed, packed, coated or layered within, on, adjacent or about the components and/or surfaces of fulcrum/implant 12 and/or implant 60. In some embodiments, spinal implant system 10 comprises a surgical device that includes a fulcrum, similar to those configurations described herein, which is integral with implant 60, separate and not attached with implant 60, and/or added to implant 60. In some embodiments, spinal implant system 10 comprises a surgical device that includes a distal fulcrum, similar to those fulcrums described herein, which includes a PEEK extension member integral and/or molded with implant 60, and the extension comprises a fulcrum engageable for simultaneous manipulation of the extension and implant 60. In some embodiments, fulcrum 12 prevents closure of the neuro-foramina aperture with simultaneous access and provides leverage manipulation of the spine during torso lift and/or sagittal adjustment during and/or after, for example, osteotomy.

Figure 21:
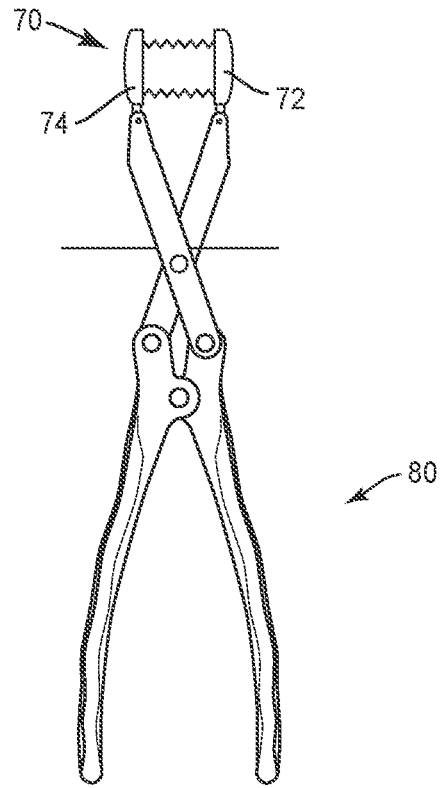
FIG. 21 is a side view of components of one embodiment of a surgical system in accordance with the principles of the present disclosure.
Figure 22:
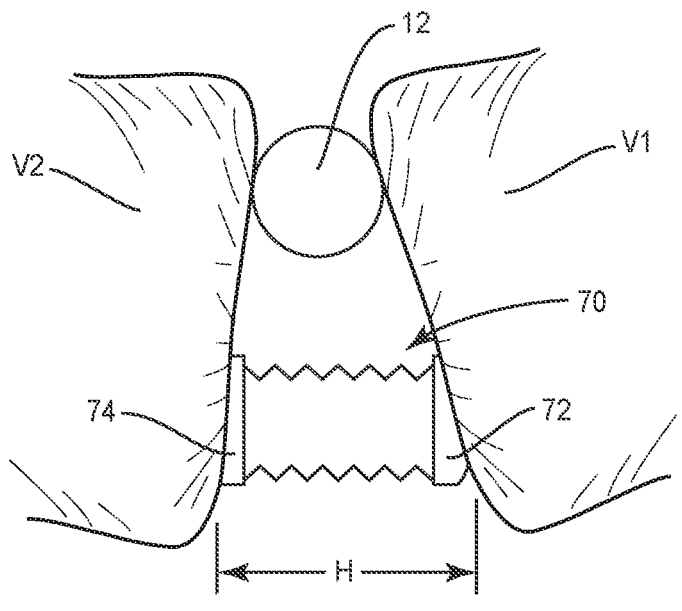
FIG. 22 is a side view of components of one embodiment of a surgical system in accordance with the principles of the present disclosure disposed with vertebrae.

In some embodiments, spinal implant system 10 includes an expandable interbody implant 70, as shown in FIGS. 21 and 22. Implant 70 includes a vertebral engaging surface 72 and a vertebral engaging surface 74. Implant 70 is disposed with vertebral space S with fulcrum/implant 12. In some embodiments, implant 70 is engageable with a surgical instrument, such as, for example, a distractor/inserter 80 to facilitate disposal of implant 70 with intervertebral space S. In some embodiments, fulcrum/implant 12 may include an expandable configuration, similar to that described herein. In some embodiments, fulcrum/implant 12 includes an expandable configuration such that after relative rotation of vertebrae V1, V2 over fulcrum/implant 12, for example, to a 10 mm height, the neuro-foramina aperture could be enlarged with an expansion of fulcrum/implant 12, for example, to an additional 12-14 mm in height. In some embodiments, fulcrum/implant 12 and/or implant 70 may comprise an expandable configuration including one or more springs, biasing elements, elastic members, plastically deformable members, hydraulic members, pneumatic members, inflatable members, shape memory members, linkages, threaded members, gears and/or instrument manipulable members to facilitate expansion.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of interbody implants, rods, tethers, plates, connectors and/or bone fasteners for use with a single vertebral level or a plurality of vertebral levels. In some embodiments, spinal implant system 10 may include one or a plurality of bone fasteners that may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A method comprising:
coupling a first implant to a first vertebra;
coupling a second implant to a second vertebra, the first vertebra and the second vertebra defining vertebrae, the first and second spinal implants being connected to one another by a spinal rod;
positioning a fulcrum between the vertebrae such that the fulcrum engages the vertebrae;
rotating the first vertebra relative to the second vertebra about the fulcrum;
inserting an interbody implant between the vertebrae, the interbody implant comprising first and second plates and a body between the plates, the body including opposite first and second ends, the first end being coupled to the first plate, the second end being coupled to the second plate, the body being expandable to increase a distance between the plates.

2. The method recited in claim 1, further comprising expanding the interbody implant to increase the distance between the plates.

3. The method recited in claim 1, wherein the first and second implants are bone fasteners.

4. The method recited in claim 1, wherein the first and second implants are bone screws.

5. The method recited in claim 1, wherein the first end is fixed to the first plate and the second end is fixed to the second plate.

6. The method recited in claim 1, wherein the fulcrum is positioned between the vertebrae such that a first surface of the fulcrum engages the first vertebra and a second surface of the fulcrum engages the second vertebra.

7. The method recited in claim 1, wherein the fulcrum is positioned between the vertebrae such that a first surface of the fulcrum directly engages the first vertebra and a second surface of the fulcrum directly engages the second vertebra.

8. The method recited in claim 7, wherein the first and second surfaces of the fulcrum are acuate.

9. The method recited in claim 7, wherein the first surface of the fulcrum is monolithically formed with the second surface of the fulcrum.

10. The method recited in claim 1, wherein rotating the first vertebra relative to the second vertebra about the fulcrum comprises:
connecting a first member to the first implant and connecting a second member to the second implant; and
moving the first member relative to the second member.

11. The method recited in claim 10, further comprising creating access to the vertebrae by creating a first surgical pathway along a first surgical approach, wherein the first member is moved relative to the second member via a second surgical approach.

12. The method recited in claim 11, wherein the second surgical approach creates a second surgical pathway.

13. The method recited in claim 11, wherein the first surgical approach includes a lateral approach and the second surgical approach includes a posterior approach.

14. The method recited in claim 11, further comprising disposing a patient in an orientation for simultaneous prone access and lateral access to the vertebrae along the surgical approaches.

15. The method recited in claim 10, wherein the first and second members are arms of a compressor.

16. The method recited in claim 10, wherein the first and second members are arms of a distractor.

17. The method recited in claim 1, wherein the fulcrum has a cylindrical cross-sectional configuration.

18. A method comprising:
coupling a first bone fastener to a first vertebra;
coupling a second bone fastener to a second vertebra, the first vertebra and the second vertebra defining vertebrae;
connecting the first bone fastener to the second bone fastener using a spinal rod;
positioning a fulcrum between the vertebrae such that the fulcrum engages the vertebrae;
rotating the first vertebra relative to the second vertebra about the fulcrum;
inserting an interbody implant between the vertebrae, the interbody implant comprising first and second plates and a body between the plates, the body including opposite first and second ends, the first end being coupled to the first plate, the second end being coupled to the second plate, the body being expandable to increase a distance between the plates.

19. A method comprising:
coupling a first bone screw to a first vertebra;
coupling a second bone screw to a second vertebra, the first vertebra and the second vertebra defining vertebrae;
connecting the first bone screw to the second bone screw using a spinal rod;
positioning a fulcrum between the vertebrae such that the fulcrum engages the vertebrae;
rotating the first vertebra relative to the second vertebra about the fulcrum;
inserting an interbody implant between the vertebrae, the interbody implant comprising first and second plates and a body between the plates, the body including opposite first and second ends, the first end being coupled to the first plate, the second end being coupled to the second plate, the body being expandable to increase a distance between the plates.

20. The method recited in claim 1, wherein the spinal rod is reduced with receivers of the implants.

* * * * *